United States Patent [19]

Jones et al.

[11] 4,438,136

[45] Mar. 20, 1984

[54] PROSTAGLANDINS

[75] Inventors: Robert L. Jones; Norman H. Wilson, both of Edinburgh, Scotland

[73] Assignee: National Research Development Corporation, London, England

[21] Appl. No.: 419,206

[22] Filed: Sep. 17, 1982

Related U.S. Application Data

[63] Continuation of Ser. No. 219,307, Sep. 3, 1980, abandoned.

[30] Foreign Application Priority Data

Jan. 5, 1979 [GB] United Kingdom ................ 7900369

[51] Int. Cl.$^3$ ..................... C07C 103/27; A61K 31/24
[52] U.S. Cl. .................................... 424/309; 424/319; 424/321; 424/263; 560/12; 560/9; 560/21; 560/22; 560/35; 560/120; 562/429; 562/430; 562/426; 562/435; 562/437; 562/440; 562/502; 546/332; 546/333; 564/80; 564/85; 564/86; 564/87
[58] Field of Search ............... 562/429, 430, 426, 435, 562/437, 440, 502; 424/309, 379, 321, 203; 560/12, 9, 21, 22, 30, 120; 546/333, 332; 564/385, 86, 87, 80

[56] References Cited

U.S. PATENT DOCUMENTS 4,073,933 2/1978 Shimomua et al. ................ 562/502

OTHER PUBLICATIONS

Fitzpatrick et al., Nature, vol. 275, pp. 764-766 (1978).
Hensby et al., Adv. in Prostaglandin & Thromboxane Research, vol. 2, p. 864.
Leeney et al., Prostaglandins, vol. 11, pp. 953-960 (1976).
Katsube et al., Agricultural and Biochemical Chem., vol. 36, pp. 1997-2004 (1972).

*Primary Examiner*—James H. Reamer
*Attorney, Agent, or Firm*—Oblon, Fisher, Spivak, McClelland & Maier

[57] ABSTRACT

Novel bicyclo [2,2,1] heptanes and hept-2-enes are substituted at the 5-position by a 6-carboxyhex-2-enyl group or a modification thereof, and at the 6-position by a grouping —C(R)=N—NHCO—(NH)$_a$—R' in which R is hydrogen, an aliphatic hydrocarbon residue, an aromatic residue or an aliphatic hydrocarbon residue substituted by an aromatic residue, a is 0 or 1 and R' is an aliphatic hydrocarbon residue, an aromatic residue, or an aliphatic hydrocarbon residue substituted directly or through an oxygen or sulphur atom by an aromatic residue. The compounds are of value for use in pharmaceutical compositions particularly in the context of the inhibition of thromboxane activity.

32 Claims, No Drawings

PROSTAGLANDINS

This is a continuation of application Ser. No. 219,307, filed Sept. 3, 1980, now abandoned.

BACKGROUND OF THE INVENTION

1. Field of the Invention

This invention relates to biologically active compounds and in particular to certain novel compounds exhibiting activity at thomboxane receptor sites.

2. Description of the Prior Art

Thromboxane $A_2$ ($TXA_2$), which is derived from arachidonic acid via prostaglandin $H_2$ ($PGH_2$), is implicated in several potentially noxious actions on various body systems, including platelet aggregation, bronchoconstriction and pulmonary and systemic vasoconstriction. Thus $TXA_2$ may be involved in the normal sealing of blood vessels following injury but in addition may contribute to pathological intravascular clotting or thrombosis. Moreover, the constrictor actions of $TXA_2$ on bronchiolar, pulmonary vascular and systemic vascular smooth muscle may be important in the development of several anaphylactic conditions including bronchial asthma. There is also some evidence to implicate $PGH_2$ and $TXA_2$ in the genesis of inflammation.

SUMMARY OF THE INVENTION

It is an object of the present invention to provide compounds having activity at thromboxane receptor sites, and most especially to provide compounds which are inhibitors of thromboxane activity and are therefore of interest in one or more areas of medical treatment including the treatment of thrombotic disorders, the treatment of anaphylactic disease states, and treatments utilising anti-inflammatory agents.

Accordingly the present invention comprises a compound being a bicyclo[2,2,1]heptane or hept-2Z-ene which is substituted at the 5-position by a 6-carboxyhex-2-enyl group or a modification thereof as defined herein, and at the 6-position by a grouping —C(R)=N—NHCO—(NH)$_a$—R' in which R is hydrogen, an aliphatic hydrocarbon residue substituted by an aromatic residue, a is 0 or 1 and R' is an aliphatic hydrocarbon residue, an aromatic residue, or an aliphatic hydrocarbon residue substituted directly or through an oxygen or sulphur atom by an aromatic residue.

DETAILED DESCRIPTION OF THE PREFERRED EMBODIMENTS

Certain of the compounds containing a modified 6-carboxyhex-2-enyl group act through the conversion of the modified group back to the unmodified group in vivo. In addition to such bioprecursors, the invention also extends in general to other pharmaceutically acceptable bioprecursors for the bicyclo[2,2,1]heptanes and hept-2Z-enes described above, such a bioprecursor being a compound having a structural formula different from the active compound but which upon administration is converted thereto in vivo.

Modifications of the 6-carboxyhex-2-enyl group which may be made in compounds according to the present invention are of two types. Firstly, there are modifications which involve alteration of the hex-2-enyl group by one, or where appropriate by a combination, of the following: (a) reduction of the double bond optionally accompanied by the replacement of a carbon atom at the 5,6 or even the 7 position relative to the $C_1$ of the carboxylic acid group by a sulphur or particularly an oxygen atom; (b) alteration of the position of the double bond, for example to the 4, 5 position; and (c) shortening or lengthening of the carbon chain, particularly by one or two methylene groups and conveniently at the end of the chain adjacent to the carboxy group.

The second form of modification, which may if desired be combined with a modification of the first type, involves conversion of the carboxy group to a functional derivative including salts thereof. Functional derivatives described in the prostaglandin art are of particular interest, including esters such as alkyl esters, amides such as those containing the group —CONH-SO$_2$CH$_3$ and variants thereon, and salts with various physiologically acceptable cations. Specific examples of salts are those with an alkali metal such as sodium or with quaternary ammonium ions or amines such as tris. As mentioned above, it will be appreciated that many of such compounds are in fact bioprecursors for the corresponding compound containing a carboxy group to which they are converted in vivo.

Groupings substituted at the 6-position in which R is not hydrogen more usually contain organic groups of a similar type to those described below for R', the aliphatic hydrocarbon and aromatic residue groups being of particular interest. Groupings in which R is hydrogen are however of particular interest.

Although the semicarbazone type of grouping, —C(R)=N—NHCO—NH—R', in which a is 1 is of interest, particular interest centres upon the acylhydrazone type of grouping —C(R)=N—NH—CO—R' in which a is 0.

Aliphatic hydrocarbon residues constituting R' may conveniently be of one to five, six, seven, eight, nine, ten or even more carbon atoms, being for example a branched or unbranched alkyl group such as methyl, ethyl, propyl, butyl, amyl, etc. Aromatic residues constituting R' are also of some interest and may be hydrocarbon or heterocyclic residues, which may be unsubstituted or substituted. The heterocyclic residues are more generally linked through a carbon atom so that residues such as pyrid-2-yl, pyrid-3-yl and pyrid-4-yl are of particular interest. Aromatic hydrocarbon residues such as phenyl are, however, of greater interest and these, and also the heterocyclic residues, may be substituted by one or more of various types of group, particularly by substituents being or containing a halogen residue (referred to hereinafter as 'a halogen substituent') for example chloro and especially fluoro, and also halogen substituted alkyl groups such as $CF_3$, but also other substituents such as sulphonamide groups which may optionally be N-substituted, amino groups which may be free or substituted, for example dimethylamino, hydroxyl groups, methoxy and other higher alkoxy groups containing alkyl groups as described above, etc. Substitution may be present at one or more of the ortho, meta and para positions of a phenyl ring or at a combination of two or more of such positions (including two similar positions), for example at the 2 and 4 positions. The order of interest in the position of substituents depends somewhat on the remaining part of the substituent group R' being o>m>p in the case of a phenoxyethyl substituent groups R' and o~p>m in the case of a benzyl substituent groups R'.

Also of interest, however, are groups R' which are aliphatic hydrocarbon residues substituted directly or through a sulphur or particularly an oxygen atom by an aromatic residue. The aliphatic residues may be of a similar size to those described above but are preferably of three atoms, particular of two atoms and especially of one atom, conveniently being branched or unbranched alkylene groups such as methylene, ethylene or propylene or corresponding trivalent groups of similar size. Similar aromatic hydrocarbon and heterocyclic residues are generally of interest for attachment to the aliphatic residues as have already been described above, the aromatic hydrocarbon residues again generally being of more interest than the heterocyclic residues. Heterocyclic residues, where used, are however of most interest when linked to the aliphatic hydrocarbon residue through the hetero atom such as in pyrid-1-yl. Substitution of an aliphatic hydrocarbon residue particularly terminally, by two or even three aromatic and/or substitution through a sulphur or particularly an oxygen atom is of some considerable interest. In case of substitution through sulphur or oxygen, the aliphatic hydrocarbon residue is conveniently of at least two carbon atoms in the case of the semicarbazone type of grouping.

Examples of specific groups R' in both acylhydrazone and semicarbazone types of grouping are:

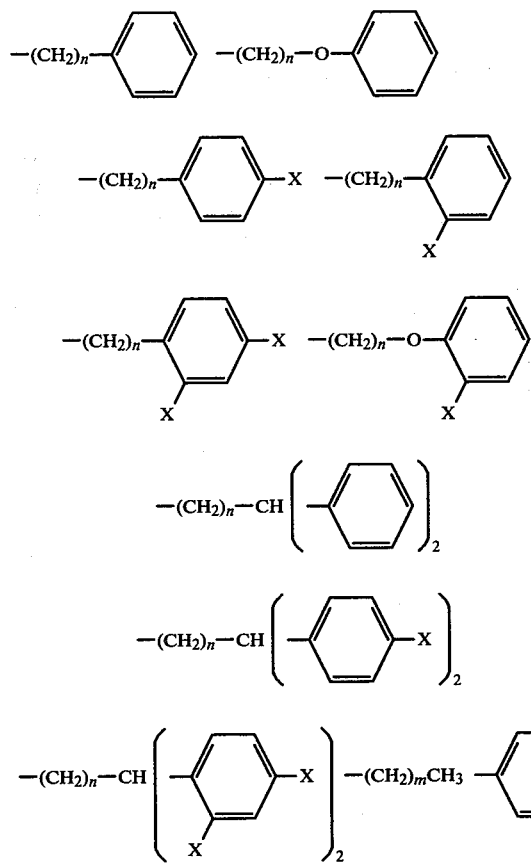

wherein n=1, 2 or 3, m=1, 2, 3, 4 or 5, and X=Cl, F or CF$_3$.

It will be appreciated that the structures of the compounds described above provide various opportunities for the occurrence of isomerism although the double bond of the unsaturated ring system is of the Z configuration. The substituents at the 5 and 6 positions of the ring may be in the cis or trans relationship to each other, compounds of the latter configuration being preferred. Moreover, as the ring system is further substituted by a divalent bridging group, then different isomers will exist which vary in which of the 5- and 6-substituents is disposed in a similar direction to the bridging group. Isomers of particular interest are (illustrated for the saturated ring system):

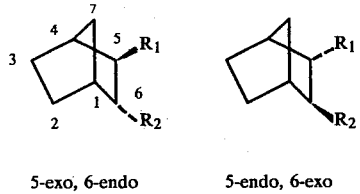

5-exo, 6-endo     5-endo, 6-exo

It will be appreciated that in this specification the formulae used to illustrate the 5-exo, 6-endo and 5-endo, 6-exo isomeric forms of compounds of this invention show one of the two enantiomers which exist, the other having a structure which is the mirror image of that illustrated, and that unless a resolution step is incorporated into the synthesis of a compound, that compound will be obtained in racemic form. Where the substituent at the 5-position is a 6-carboxyhex-2-enyl group or a group modified therefrom but still containing the double bond then the configuration about this bond is preferably cis (Z) rather than trans (E). In the second substituent at the 6-position, although syn and anti isomerism is possible about >C=N-double bonds the isomers are often readily interconvertible at room temperature and exist as a mixture which shows biologically activity that may, however, derive predominantly from one isomer. In addition to the foregoing isomerism, the compounds of the present invention will generally be resolvable into enantiomeric forms and one among these may be preferred by virtue of biological activity or physical properties.

Examples of specific compounds according to the present invention are:

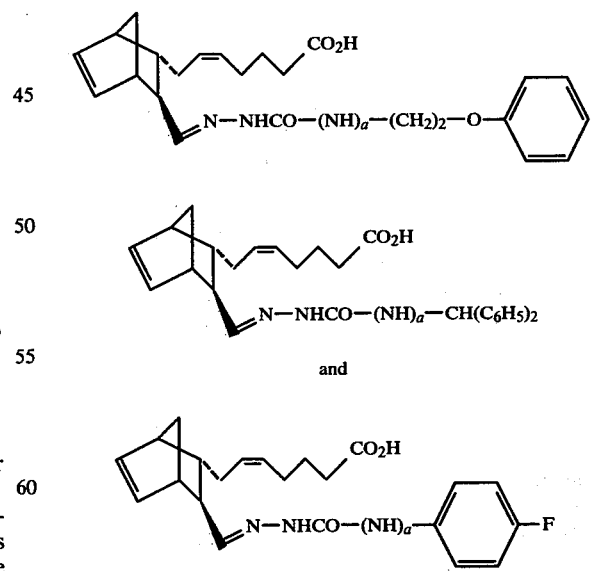

and its chloro and trifluoromethyl analogues, as well as the ring saturated analogues of these compounds.

Compounds according to the present invention may conveniently be prepared by using as a starting material a compound containing the unsaturated ring system and having substituents on the ring system which are suitable precursors for those in the final compound. The formation of such an unsaturated bicyclic ring system is conveniently effected by means of a Diels Alder reaction. Compounds containing the saturated ring system are conveniently produced by reduction of the ring double bond, for example by the use of hydrogen in the presence of a charcoal, such as palladium-charcoal. Such reduction more usually being effected prior to modification of the substituents. A convenient starting material providing suitable precursors for the final substituents is a maleinaldehydic acid pseudo ester of formula

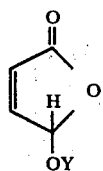

wherein Y represents a hydrocarbon residue, preferably an aliphatic residue such as methyl or especially ethyl. Following reaction of this compound with cyclopentadiene in a Diels Alder reaction, modification of the substituents provided by the ester is effected, conveniently to give initially a 6-carboxyhex-2-enyl group or a modification thereof and a formyl group, —CHO, which may readily be modified further as desired.

An example of such a procedure is shown in the reaction scheme at the end of this specification, following the Examples. (the numbering of compounds corresponding to that used in Example 1 and which has also been followed in Example 2 for the ring unsaturated analogue and the following abbreviations are employed in the scheme: Ts, toluene sulphonyl: DMSO, dimethyl sulphoxide; Et, ethyl: Bu, butyl). The use of ethoxycarbonyl rather than methoxycarbonyl groups and of ethyl rather than methyl acetal groups has been found to be of value in this procedure. In the final stages of the procedure the acetal group of compound (8) is converted to a formyl group to give compound (9) or compound (9'), and this formyl group is reacted with a suitable reagent or reagents to introduce the appropriate acylhydrazone or semicarbazone type of group, the carboxy group of the 6-carboxyhex-2-enyl group optionally being protected during this procedure thereby generally giving a slightly greater yield.

The introduction of both types of group may be effected by the action of a suitable reagent either directly with the formyl group in the case of compounds in which R is hydrogen or with the carbonyl group produced through the action of a Grignard reagent on the formyl group (and the subsequent oxidation of the secondary alcohol so formed, for example using the Jones reagent), in the case of compounds in which R is an aliphatic, aromatic or araliphatic residue. The reagent may conveniently take the form of a hydrazide $H_2N—NHCOR'$, or a semicarbazide, $H_2N—NH—CONHR'$, respectively. As indicated above, it is possible either to react such a reagent, for example p-fluorobenzoic acid hydrazide or phenyl semicarbazide, with the compound (9) or with a corresponding compound in which the carboxy group is protected. Such a protected compound is conveniently obtained from the compound (8), for example by reaction with diazomethane followed by treatment with aqueous acid to give compound (9'). Following reaction of the reagent with the formyl group, the carboxy group is deprotected, for example by deesterification using $KOH/CH_3OH/H_2O$. A similar choice with regard to the nature of the 5-substituent present in the reactant exists when the 6-substituent is a group in which R is other than hydrogen.

Modification of the 6-carboxyhex-2-enyl group may be effected through the initial introduction of a modified group or by modification of this group during or at the end of the sythesis, ester formation conveniently being effected, for example at the stage indicated hereinbefore and amides similarly being prepared by conventional procedures. Indeed, the procedures for effecting the various modifications indicated above will be apparent from the considerable literature existing on prostaglandin chemistry. Thus, for example, one convenient route for the preparation of compounds containing a 6-carboxyhexyl group involves in the case of the bicyclo[2,2,1]heptanes a delay in the reduction step used to produce a saturated ring still compound (8) has been obtained when saturation of both the double bond in the ring and that of the 6-carboxyhex-2'2-enyl group may be effected. In the case of the bicycle[2,2,1]hept-2Z-enes the corresponding 5-(6'-carboxyhexyl),6-formyl compound may be obtained by the Diels Alder reaction of 8-carboxy-1-formyl-oct-1-ene and cyclopentadiene (a separation of the trans isomers obtained being required).

It will be appreciated that the methods described above are not the only ones which may be used for the preparation of compounds according to the present invention and that various alternative procedures may be used as will be apparent to those skilled in the art of prostaglandin chemistry.

It has been found that compounds according to the present invention inhibit the aggregatory activity of 15S-hydroxy-11α-9α(epoxymethano)-prosta-5Z,13E-dienoic acid[11,9-(epoxymethano) $PGH_2$], which is a stable $TXA_2$ mimic, on human platelets in vitro. It is believed that such inhibition is the result of the compounds being thromboxane antagonists and the activity of the compounds is for convenience hereinafter discussed in these terms. Preferred compounds according to the present invention exhibit a pure antagonist activity. The related compounds described and claimed in our copending application Ser. No. 431,554 filed Sept. 30, 1982 of even date herewith in which the grouping =N—NHCO—$(NH)_a$— in the present compounds is replaced by the grouping =N—O— have been found to show a partial agonist activity in certain tests, such as in the test based on the contractile activity of 11, 9-(epoxymethano) $PGH_2$ on the rabbit aorta strip, although they are antagonists in the platelet test. Structural features which tend to endow these compounds with a more pure antagonist form of activity are described in that application. It has been found, however, that the compounds of the present invention generally show little tendency to deviate from pure antagonist activity. Activity has also been observed on compounds according to the present invention on guinea pigs tracheal muscle.

Preferred compounds such as 5-endo-(6'-carboxyhex-2'Z-enyl)-6-exo-(N-p-fluorobenzoyl-hydrazonomethyl)-bicyclo[2,2,1]heptane (in which the substituent at the six position may alternatively be identified as a N-p-fluorobenzamido-carboxaldimine or N-(p-fluorobenzamido)-iminomethyl group) and 5-endo-(6'-carboxyhex-2'Z-enyl)-6-exo-[N-(phenylcarbamoyl)-hydrazonomethyl]-bicyclo[2,2,1]heptane (in which the substituent at the six position may alternatively be identified as a N-phenylureidocarboxaldimine or N-(phenylureido)-iminomethyl group) are antagonists in the platelet test, block the aggregatory action of archidonic acid which is converted to $TXA_2$ by the platelet enzyme system and may or may not block the aggregatory action of ADP which acts via non-$TXA_2$ sensitive systems. Moreover, they are pure antagonists in the rabbit aorta strip test but do not block the contractile action of noradrenaline which acts on α-adrenoceptors.

Compositions according to the present invention are of interest for the treatment of thrombotic disorders and also for the treatment of anaphylacetic disease states, for example as bronchodilators for the treatment of asthma, etc. They additionally have potential an anti-inflammatory agents. It will be appreciated that the spectrum of activity shown by any particular compound will vary and that certain compounds may be of particular interest in one of these applications whilst other compounds are of particular interest in another of them. Modifications of a compound can have other advantages. Thus, for example, it has been found that the ring unsaturated compounds described herein are usually less stable than the ring saturated compounds although the latter have similar activity in general. Furthermore the use of esters and other derivatives of the 6-carboxyhex-2-enyl group can have advantages in relation to slow release depot preparation through conversion in vivo to the active compound containing a free carboxy group, although the low water solubility of the esters must be taken account of.

The compounds may be formulated for use as pharmaceuticals for both animal and particularly human administration by a variety of methods, but usually together with a physiologically acceptable diluent or carrier. The compounds may, for instance, be applied as an aqueous or oily solution or suspension or as an emulsion for parenteral administration, the composition therefore preferably being sterile and pyrogen-free. The preparation of aqueous solutions of compounds in which the 5-substituent terminates in a free carboxy group may be aided by salt formation. The compounds may also be compounded for oral administration in the presence of conventional solid carrier materials such as starch, lactose, dextrin and magnesium stearate. Alternative formulations are as aerosols, suppositories, cachets, and, for localised treatment, as suitable creams or drops. Without comment to a rigid definition of dosage, which is difficult in view of the different levels of activity, methods of formulation, and methods of administration, some general guidance may be given. In the case of systemic administration to produce a thromboxane antagonism the normal daily dosage which is proposed lies in the range from about 0.1 mg to about 10 mg per kilogram (the average weight of a human being about 70 kg) and particularly from about 1 mg to about 5 mg per kilogram. It will be appreciated, however, that dosages outside this range may be considered, and that the daily dosage may be divided into two or more portions.

The invention is illustrated by the folllowing Examples.

The compounds of the present invention are related to the compounds described and claimed in our copending application Ser. No. 431,554 filed Sept. 30, 1982, of even data herewith in which the grouping =N—NH—CO—(NH)$_a$— in the present compounds is replaced by the grouping =N—O—. Further specific examples of variations which may be effected in the common parts of the molecule are to be found in that application. Although the compounds have predominantly the isomeric form indicated, some minor contamination by other isomers, particularly the 5-endo, 6-endo isomer, may be present. The various compounds are all obtained in racemic form.

The numbering used for the sub-sections of Example 1 is in accordance with that used in the reaction scheme at the end of this specification, following the Example. In Example 2, sub-sections relating to the analogous ring unsaturated compounds have been similarly numbered.

EXAMPLE 1

5-endo-(6'-Caboxyhex-2'Z-enyl)-6-exo-(N-p-fluorobenzoylhydrazonomethyl)-bicyclo[2,2,1]heptane (1) Maleinaldehydic acid pseudo-ethyl ester 30 g of redistilled furan-2-aldehyde is mixed with 600 ml dry ethanol and 300 mg of methylene blue is added. Dry air is blown gently through the solution and the material is irradiated with a 300 W tungsten lamp for about two days until t.l.c. in a silica gel/ether system shows essentially no remaining starting material. The solution is then stirred with vanadium pentoxide for four hours, filtered, and the solvent removed under reduced pressure. The residual oil is distilled under high vacuum to give the title compound as an oil (23.6 g, 76%), b.p. 90°–92° C./0.2 mm.

(2) Diels Alder reaction between maleinaldehydic acid pseudoethyl ester and cyclopentadiene Freshly cracked cyclopentadiene (9.0 g) is mixed with 11.0 g of the pseudo ester (1). A gentle warming is observed and the mixture is allowed to stand overnight. The N.M.R. spectrum typically shows the formation of the adduct (2) to be complete and the material is taken to the next step without purification.

(3)
5-endo-Ethoxycarbonyl-6-exo-diethoxymethyl-bicyclo-[2,2,1]-hept-2Z-ene

The Diels-Alder adduct (2) (10 g) is heated in a mixture of triethyl orthoformate (10 ml), dry ethanol (100 ml), and concentrated sulphuric acid (1 ml). The mixture darkens and after 12 hours is cooled and treated with anhydrous potassium carbonate (5 g) and ether (150 ml). Water is then slowly added with efficient mixing to neutralise the acid. The product is extracted with ether, washed with water and distilled to give the title compound as an oil (7.3 g, 63%, b.p. 115°–120° C./0.3 mm.

(4)
5-endo-Ethoxycarbonyl-6-exo-diethoxymethyl-bicyclo[2,2,1]heptane 5-endo-Ethoxycarbonyl-6-exo-diethoxymethyl-bicyclo[2,2,1]hept-2-ene (30 g) is dissolved in 200 ml of ethanol and 0.3 g of 10% palladium on charcoal is added. The mixture is vigorously stirred in 1 atmosphere of hydrogen gas at room temperature. 1 molar equivalent of hydrogen gas is absorbed and the product is then isolated by removal of the catalyst by filtration through a Celite pad, followed by evaporation of the filtrate to give a quantitative yield of the title compound as an oil b.p. 105°–110° C./1.5 mm.

(5)
5-endo-Hydroxymethyl-6-exo-diethoxymethyl-bicyclo[2,2,1]heptane

The ester (4) (27 g) is added in ether to a 10% excess of lithium aluminium hydride (2.1 g) in ether with stirring at reflux temperature. The mixture is boiled for 1 hour after the addition and is then quenched by the addition of wet ether followed by 5% aqueous sodium hydroxide to precipitate aluminium salts. The colourless organic phase is dried over magnesium sulphate, filtered and evaporated to give the title compound as an oil (20 g, 91%).

(6)
5-endo-Cyanomethyl-6-exo-diethoxy-bicyclo[2,2,1]heptane

The alcohol (5) (20 g) in a minimum volume of dry pyridine is added slowly to 20 g of p-toluenesulphonyl chloride in 130 ml dry pyridine with stirring at 0° C. The mixture is kept at 5° C. overnight and then poured into a water-ice mixture. The resulting precipitate is filtered off and dried to give the tosylate ester of the alcohol in 85% yield as an off-white solid, mp 84°–86° C. (dec.).

The tosylate (14 g) in 15 ml dimethyl sulphoxide is added to 5 g of dry potassium cyanide in 20 ml dimethyl sulphoxide. The mixture is stirred under nitrogen and the temperature slowly raised over 1 hour to 110° C. After 5 hours the reaction mixture is cooled and poured into water. The product is isolated by ether extraction, and purified by distillation to give the title compound (7.8 g, 90%), b.p. 115°–126° C./1.5 mm.

(7)
6-exo-Diethoxymethyl-5-endo-formylmethyl-bicyclo[2,2,1]heptane

The cyano compound (6) (20 g) is stirred at −15° C. in 200 ml dry toluene under nitrogen. Di-isobutylaluminium hydride (113 ml of a 1 M solution in hexane) is added to the substrate over 25 minutes and the mixture allowed to reach room temperature. After 1 hour, methanol (30 ml) is cautiously added, followed by 400 ml of saturated aqueous sodium hydrogen tartrate. The mixture is stirred and heated at 40° C. for 2 hours. The upper organic layer is separated and the aqueous phase further extracted with ethyl acetate. The combined organic solutions are dried (Mg SO$_4$) and the solvent removed to give a yellow oil. This is chromatographed on Florisil in benzene to give the pure title compound as a colourless oil (17.2 g, 85%) ($\nu_{max}$(film): 1725 cm$^{-1}$.

(8)
5-endo-(6'-Carboxyhex-2'Z-enyl)-6-exo-diethoxymethyl-bicyclo[2,2,1]heptane (4-carboxy-n-butyl)-triphenylphosphonium bromide (23.3 g) is dried at 75° C. under vacuum for 2.5 hours. The resulting white solid is then cooled, the vacuum released to dry nitrogen, and 30 ml of dimethyl sulphoxide is added. A 2 M solution of dimesyl sodium in dimethyl sulphoxide (50 ml) is added slowly while the mixture is maintained at 25° C. with a water bath. After 15 minutes the aldehyde (7) (5.0 g) is added to the deep red ylide thus produced. The mixture is stirred overnight and then the solvent is removed at 55°–60° C. under vacuum. The residue is dissolved in water, and the aqueous phase is extracted with ether and then carefully acidified to pH 4 with 2 N HCl. The precipitate is extracted into ether and the ethereal solution is dried and concentrated to give the title compound as an oil (3.7 g, 55%).

(9)
5-endo-(6'-Carboxyhex-2'Z-enyl)-6-exo-formyl-bicyclo[2,2,1]heptane

The acid acetal (8) (1.8 g) is dissolved in 200 ml chloroform and 50 ml of concentrated hydrochloric acid is added to form a two phase system. The mixture is vigorously stirred for 90 minutes and is then extracted with ether and the ethereal solution dried and concentrated. The residual oil is purified by silicic acid chromatography, the oil being applied to the column (prepared by slurrying 10 g of Unisil silicic acid—Clarkson Chemical Co., USA—in hexane and pouring into a glass chromatography column) in hexane and elution being carried out with increasing proportions of diethyl ether in hexane up to pure diethyl ether. The chromatography gives the title compound as a colourless oil (1.4 g, 83%), $\nu_{max}$(film): 795,1715 (broad), 2700 cm$^{-1}$; δ(90 mHz, CDCl$_3$) 1.2 to 2.6 (18H,m), 5.4 (2H,m), 9.6 (1H,d). Note: Care should be taken to avoid contact of this compound with methanol since it very readily forms a dimethyl acetal.

(10)
5-endo-(6'-Carboxyhex-2'Z-enyl)-6-exo-(N-p-fluorobenzoylhydrazonomethyliminomethyl)-bicyclo[2,2,1]heptane The aldehyde acid (9) (100 mg) is heated with p-fluorobenzoic acid hydrazide (40 mg) in tetrahydrofuran (5 ml) for 1.5 hours at 40° C. The solvent is then evaporated and the residual oil is purified by silicic acid chromatography, the oil being applied to the column (which is prepared by slurrying 10 g of Unisil silicic acid—Clarkson Chemical Co., USA—in hexane and pouring into a glass chromatography column) in hexane and elution being carried out with increasing proportions of diethyl ether in hexane up to pure diethyl ether. The chromatography gives the title compound as an oil (27 mg) which is not readily soluble in ether, $\lambda_{max}$(C-H$_3$OH) 254 nm, $\epsilon_{max}$ 12,350. The methyl ester trimethylsilyl ether derivative runs as a single peak on gas chromatography mass spectroscopy and has M+ 472.

The p-fluorobenzoic acid hydrazide is prepared as follows. Ethyl p-fluorobenzoate (8.4 g) is refluxed with hydrazine hydrate (3.75 g) for 3 hours. The mixture is then cooled, ether is added and the precipitate of p-fluorobenzoic acid hydrazide (3.2 g) is removed by filtration, washed with ether and desiccated, m.p. 149°–151° C.

EXAMPLE 2
5-endo-(6'-Carboxyhex-2'Z-enyl)-6-eno-(N-p-fluorobenzoylhydrazonomethyl)-bicyclo[2,2,1]hept-2Z-ene

(1), (2), (3)
5-endo-Ethoxycarbonyl-6-exo-diethoxymethyl-bicyclo[2,2,1]hept-2Z-ene Maleinaldehydic acid pseudo-ethyl ester is prepared as described in Example 1 (1) and reacted with cyclopentadiene in a Diels Alder reaction as described in Example 1 (2). The Diels Alder adduct is treated with ethanol under acidic conditions as described in Example 1 (3) to give 5-endo-ethoxycarbonyl-6-exo-diethoxymethyl-bicyclo[2,2,1]hept-2Z-ene (3).

(5)
5-endo-Hydroxymethyl-6-exo-diethoxymethyl-bicyclo[2,2,1]hept-2Z-ene

The ester (3) is added in ether to lithium aluminium hydride (10% excess) in ether with stirring at reflux temperature. After the addition, the mixture is boiled for a further 1 hour. The reaction is quenched with wet ether and then 5% aqueous sodium hydroxide to precipitate aluminium. The colourless organic phase is filtered, dried over anhydrous potassium carbonate, and the resulting alcohol (85–90% yield) used directly in the next stage.

(6)
5-endo-Cyanomethyl-6-exo-diethoxymethyl-bicyclo[2,2,1]hept-2Z-ene

The alcohol (5) (7 g) in 15 ml dry pyridine is added slowly at 0° C. to p-toluenesulphonyl chloride (7.5 g) in pyridine (45 ml). The mixture is kept overnight at 10° C. and then quenched by pouring over ice with vigorous shaking. The product is extracted with ether, washed consecutively with water, 0.1 M sodium carbonate and brine, and then dried ($K_2CO_3$) and the solvent removed to give the tosylate ester of the alcohol as a colourless oil in high yield.

The tosylate ester (12 g) in dimethyl sulphoxide (15 ml) is added with stirring to potassium cyanide (3 g) in dimethyl sulphoxide (20 ml). The mixture is heated to 100° C. under nitrogen for 6 hours and is then cooled, poured into water and the product taken into ether. The solvent is removed and the residue distilled to give title compound as an oil (6.6 g, 88%), b.p. 112°–124° C./1.8 mm.

(7)
6-exo-Diethoxymethyl-5-endo-formylmethylbicyclo[2,2,1]hept-2Z-ene

This aldehyde is prepared from the cyano compound (6) analogously to the ring saturated compound of Example 1 and as described in full in applicants' copending application Ser. No. 431,554 filed Sept. 30, 1982.

(8)
5-endo-(6'-Carboxyhex-2'Z-enyl)-6-exo-diethoxymethyl-bicyclo[2,2,1]hept-2Z-ene (4-Carboxy-n-butyl)-triphenylphosphonium bromide (7.0 g) is dried at 75° C. under vacuum for 90 minutes. The white solid is cooled, the vacuum is released to dry nitrogen and 10 ml of dimethyl sulphoxide (10 ml) is added followed by 15 ml of a 2 M solution of dimesyl sodium in dimethyl sulphoxide. The temperature is maintained at 25° C. and the aldehyde (7) (1.5 g) is added to the deep red ylide solution. After stirring overnight the solvent is removed at 55°–60° C. under vacuum. The residue is dissolved in water, extracted with ether, and the aqueous phase carefully acidified to pH 4 with 2 N HCl. The mixture is extracted with ether and the ethereal solution dried and concentrated to give the title compound as an oil (1.34 g, 66%).

(9')
5-endo-(6'-Methoxycarbonylhex-2'Z-enyl)-6-exo-formyl-bicyclo[2,2,1]hept-2Z-ene The acid acetal (8) (5 g) in ether is treated with excess etheral diazomethane to form the methyl ester and then the ketal protecting group is removed by dissolving the compound in 215 ml chloroform and adding concentrated hydrochloric acid (55 ml) to form a two-phase system. The mixture is vigorously stirred for 90 minutes, the reaction being followed by g.l.c. to check on completion. The mixture is extracted with ether and the ethereal solution dried and concentrated to give the title compound as an oil (3.38 g, 90%).

(10')
5-endo-(6'-Methoxycarbonylhex-2'Z-enyl)-6-exo-(N-p-fluorobenzoylhydrazonomethyl)-bicyclo[2,2,1]hept-2Z-ene The aldehyde ester (9') (100 mg) is heated with p-fluorobenzoic acid hydrazide (40 mg) in tetrahydrofuran (5 ml) for 1.5 hours at 40° C. The solvent is then evaporated and the residual oil is purified by silicic acid chromatography, the oil being applied to the column (which is prepared by slurrying 10 g of Unisil silicic acid—Clarkson Chemical Co., USA—in hexane and pouring into a glass chromatography column) in hexane and elution being carried out with increasing proportions of diethyl ether in hexane up to pure diethyl ether. The chromatography gives the title compound as an oil.

(10)
5-endo-(6'-Carboxyhex-2'Z-enyl)-6-exo-(N-p-fluorobenzoylhydrazonomethyl)-bicyclo[2,2,1]hept-2Z-ene Ester cleavage in compound (10') is effected by heating in aqueous methanol with potassium hydroxide (0.1 N) for 3 hours at 40° C. The product is again purified by silicic acid chromatography, using a 10 g Unisil silic acid column made up in hexane and eluting with increasing proportions of diethyl ether in hexane up to pure diethyl ether. The chromatography gives the title compound as an oil.

EXAMPLE 3
5-endo-(6'-Carboxy-2'Z-enyl)-6-exo-[N-(phenylcarbamoyl)-hydrazonomethyl])-bicyclo[2,2,1]heptane 5-endo-(6'-carboxyhex-2'Z-enyl-6-exo-formyl-bicyclo[2,2,1]heptane [100 mg; prepared as described in Example 1(9)] is heated with phenyl semicarbazide (80 mg) in tetrahydrofuran for 2 hours at 40° C. The solvent is then evaporated and the residue purified by silicic acid chromatography as described under Example 1 (10) followed by liquid-gel partition chromatography using a 400×15 mm column of Sephadex LH20 substituted with Nedox 1114 olefin oxide to 20% w/w and eluting with dichloroethane/hexane/ethanol (100:100:5 v/v/v) containing 0.1% v/v of acetic acid at a flow rate of 12 ml/hour. The chromatography gives the title compound as an oil (64 mg), $\lambda_{max}$ ($CH_3OH$) 248.5 nm, $\epsilon_{max}$ 23,500.

The phenyl semicarbazide is prepared as follows. Ethyl-N-phenyl carbamate (8.25 g) is refluxed with hydrazine hydrate (3.75 g) for 3 hours. The mixture is evaporated to dryness and the residue is treated with ether, and the solid phenyl semicarbazide (1.5 g) is filtered off, washed with ether and dessicated, m.p. 122°–124° C.

EXAMPLE 4

5-endo-(6'-Carboxyhex-2'Z-enyl)-6-exo-[1'-(p-fluorobenzoylhydrazono)-ethyl])-bicyclo[2,2,1]heptane (1)

5-endo(6'-Carboxyhex-2'Z-enyl)-6-exo-(1'-hydroxyethyl) bicyclo[2,2,1]heptane 5-endo-(6'-Carboxyhex-2'Z-enyl)-6-exo-formyl bicyclo[2,2,1]heptane is prepared as described in Example 1 (9). This aldehyde (250 mg, 1 mmole) is dissolved in dry tetrahydrofuran (10 ml) at 0° C. and treated under nitrogen and with stirring over 30 minutes with a 1 M solution of methyl magnesium iodide in ether (2 ml). The mixture is stirred under nitrogen overnight whilst it is allowed to come to room temperature. The reaction is then quenched by the addition of dilute aqueous hydrochloric acid and the product is extracted with ether (3x), the ether solution is dried and evaporated to give the title compound as an oil (200 mg). A small sample is treated to form the methyl ester trimethylsilyl ether and on gas chromatography mass spectroscopy on a 3% OVI column this shows a carbon value of 18.2, a M+ value of 352 and a base peak of 117.

Chromatography on a column of Sephadex LH 20 substituted with Nedox 1114 olefin oxide to 20% w/w (Lipidex) of the bulk of the oily product using a mixture of (all proportions by volume) 100 parts of hexane, 100 parts of 1,2-dichloroethane, 5 parts of ethanol and 0.1% of the total of glacial acetic acid, as eluant yields the two isomeric secondary alcohols differing in the configuration at the newly introduced asymmetric carbon atom (—CHOH.CH$_3$). Nmr spectroscopy on these isomeric products in CDCl$_3$ gives the following δ values: First isomer eluted: 7.3 (s. broad, 1H, O$\underline{H}$); 5.45 (m., 2H, olefinic H); 3.6 (m-qxd: 1H, —C$\underline{H}$OH), 2.5–1.0 (m;, 21.H, aliphatic H). 1.2 (d, C$\underline{H}_3$ discernible).

Second isomer eluted: 7.8 (s. broad, 1H, O$\underline{H}$); 5.4 (m., 2H, olefinic H); 3.55 (m-qxd, 1H, C$\underline{H}$OH); 2.5–1.0 (m, 18H, aliphatic H); 1.2 (d, C$\underline{H}_3$ discernible).

(2)

5-endo(6'-Carboxyhex-2'Z-enyl)-6-exo-acetyl-bicyclo[2,2,1]heptane

The procedure described under (1) is repeated with 600 mg of the aldehyde to give a mixture of the two isomeric alcohols (500 mg). This mixture is dissolved in pure acetone (15 ml) and the solution is cooled to 0° C. Jones reagent (600 μl of a solution prepared by dissolving 26.7 g of chromic anhydride in 23 ml of concentrated sulphuric acid and diluting to 100 ml with water, followed by filtration) is added slowly to the cooled solution with vigorous stirring over 15 minutes. After a further 10 minutes stirring at 0° C. the mixture is poured into water and the product extracted with ether. The ether solution is dried and evaporated to give the title compound as an oil (about 75% overall yield from formyl compound). G.C.M.S. (3% OVI) on the methyl ester gives a carbon value of 17.15, a M+ value of 278 and a base peak of 43/137. Nmr spectroscopy in CDCl$_3$ gives the following δ values: 10.0 (s -broad, 1H, COOH); 5.4 (m,2H, olefinic H); 2.8–1:1 (m 21H, aliphatic H); 2.2 (s, CH$_3$—CO, discernible).

(3)

5-endo-(6'-Carboxyhex-2'Z-enyl)-6-exo-(1'-(p-fluorobenzoylhydrozono)-ethyl-bicyclo[2,2,1]heptane The ketone (2) is reacted with p-fluorobenzoic acid hydrazide in dry pyridine according to the procedure described in Example 1 (10) and the reaction mixture worked up as described therein to give the title compound.

Note: In a variation of the procedure described above the reaction with p-fluorobenzoic acid hydrazide in pyridine under (3) is replaced by reaction with phenyl semicarbazide in tetrahydrofuran as described in Example 3 to give the corresponding compound containing a 6-exo-{1'-(N-phenylcarbamoyl)-hydrazono)-ethyl} substituent.

Example 5

5-endo(6'-Carboxyhex-2'Z-enyl)bicyclo[2,2,1]heptanes containing other 6-exo substituents The additional compounds of formula

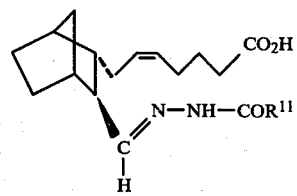

listed in Table 1 below are prepared as described in Example 1 using the appropriate hydrazide. For the purposes of comparison data on the compounds of Examples 1 and 3 has also been included in this table. The free acids may, if desired, be converted to the methyl esters by solution in methanol, using warming and the addition of NaHCO$_3$ as necessary, followed by the addition of an excess of ethereal diazomethane to the methanolic solution, standing, and the removal of the solvent.

The UV data relates to the main peak(s) of the spectrum in methanol and the MS data relates to values obtained by direct inlet.

TABLE 1

| R'' | U.V. Data $\lambda_{max}$ nm | $\epsilon_{max}$ | M.S. Data M+ |
|---|---|---|---|
| —⟨⟩—F | 254 | 12,350 | 386 |
| —⟨⟩—OCH$_3$ | 267.5 | 22,400 | 398 |
| —⟨⟩—N(CH$_3$)$_2$ | 317 | 23,200 | 411 |
| —CH$_2$—⟨⟩ | 233 | 14,300 | 382 |
| —CH—(⟨⟩)$_2$ | 236 | 13,150 | 458 |

TABLE 1-continued

| R″ | U.V. Data λmax nm | εmax | M.S. Data M+ |
|---|---|---|---|
| —CH₂—CH—(C₆H₅)₂ | 219 235 | 22,650 15,400 | 472 |
| —CH₂—O—C₆H₅ | 220 | 16,050 | 398 |
| —(CH₂)₃CH₃ | 233.5 | 13,400 | 348 |
| —NH—C₆H₅ | 248.5 | 23,500 | 383 |

N.m.r. data on the majority of the compounds of Table 1 is presented in Table 2 below. All of the values relate to CDCl₃ solution and are referred to (CH₃)₄Si.

The term "carbimino proton" is used to identify that proton attached to the carbon atom joined to the 6-position of the ring whilst the term "hydrazono proton" is used to identify the proton of the =N—NH— group.

TABLE 2

| Compound R″ | Ethylenic protons in substituent of 5-position of ring | Carbimino proton | Hydrazono proton[1] | Protons in R″ |
|---|---|---|---|---|
| —C₆H₄—F | 5.35 (m) 2H | obscured by aromatic H | 7.6 (br)1H | 7.1(m), 7.9(m) } 4H |
| —C₆H₄—OCH₃ | 5.35 (m) 2H | obscured by aromatic H | 7.6(br)1H | 3.8(s)3H, 6.9(m), 7.9(m) } 4H |
| —C₆H₄—N(CH₃)₂ | 5.35 (m) 2H | 7.45(d)1H | 6.2(br)1H | 3.05(s)6H, 6.65(m), 7.80(m) } 4H |
| —CH—(C₆H₅)₂ | 5.30 (m) 2H | 7.2(d)1H | not detected | 6.0(m)1H, 7.4(m)10H |
| —CH₂—CH—(C₆H₅)₂ | 5.35 (m) 2H | 7.00(d)1H | not detected | 3.4(d)2H, 4.7(t)1H, 7.25(m)10H |
| —CH₂—O—C₆H₅ | 5.35(m)2H | obscured by aromatic H | not detected | 4.60(s)2H, 6.85–7.50(m)4H |
| —(CH₂)₃CH₃ | 5.40(m)2H | 7.15(d)1H | 8.8(br)1H | 2.7(t)2H, 0.95(t)3H |
| —NH—C₆H₅ | 5.35(m)2H | obscured by aromatic H | 8.05(br)1H | 9.7(br)1H, 7.0–7.6(m)5H |

[1]The hydrazono proton is always broad and in some cases the broadening is such that the signal cannot be detected.

Example 6
5-endo-(6′-Carboxyhexyl)-6-exo-(N-phenylcarbamoyl)-hydroazonomethyl)-bicyclo[2,2,1]heptane (1)
5-endo-(6′-Carboxyhexyl)-6-exo-formyl-bicyclo[2,2,1-]heptane 5-endo-(6′-Carboxyhex-2′Z-enyl)-6-exo-diethoxymethylbicyclo[2,2,1]heptane is prepared as described in Example 1(8). This acid/acetal (300 mg) is stirred with 10% palladium charcoal (50 mg) in absolute ethanol (10 ml) for 30 minutes whilst continuously passing hydrogen gas through the suspension. The catalyst is removed by filtration through a Whatman No. 50 filter disc and the ethanol is then removed in vacuo. The oily residue of 5-endo-(6′-carboxyhexyl)-6-exo-diethoxymethylbicyclo[2,2,1]heptane is dissolved in CHCl₃ (50 ml), 2 N aqueous hydrochloric acid (50 ml) is added, and the two phase system is stirred for 6 hours at room temperature. Water (100 ml) is then added, followed by diethyl ether (150 ml) and after vigorous shaking the organic phase is separated. The aqueous phase is extracted with a further 150 ml of diethyl ether and the two ether extracts are combined. Evaporation of the diethyl ether from the dried solution gives 5-endo(6'-carboxyhexyl)-6-exoformyl-bicyclo[2,2,1]heptane as an oil (152 mg), $\nu_{max}$(film) 1715 cm$^{-1}$(broad); M.S. (methyl ester): M$^+$/m$^+$+1 266/267-single peak; δ (CDCl$_3$) 1.1–2.6 (22H, aliphatic H), 9.6 (d, 1H, CHO), 10.0 (broad, COOH).

(2)

5-endo-(6'-Carboxyhexyl)-6-exo-(N-(phenylcarbamoyl)-hydrazonomethyl)bicyclo[2,2,1]heptane The aldehyde/acid (1) (50 mg) is reacted in tetrahydrofuran with phenyl semicarbazide according to the procedure described in Example 3 and the reaction mixture is worked up according to the procedure described therein to give the title compound as an oil (48 mg, 63%, after chromatography), $\lambda_{max}$ (CH$_3$OH) 248 nm, $\epsilon_{max}$ 15,750; MS (direct inlet on free acid): M$^+$385.

Example 7: Tests of Biological Activity

Various of the compounds described in Examples 1 to 3 are tested for biological activity in the human platelet and rabbit aorta systems.

Human Platelet System

Platelet-rich plasma is obtained from fresh, citrated human blood. Addition of the 11,9-epoxymethano analogue of PGH$_2$ (1×10$^{-7}$ to 5×10$^{-7}$ M) causes immediate aggregation recorded as an increase in light transmission (600 nm). In a second experiment the individual compounds are added 5 minutes previously to addition of the PGH$_2$ analogue. The dose of the PGH$_2$ analogue added is then increased to a level which gives a similar response to that obtained in the absence of antogonist. The affinity constant, K$_B$, for the compound is calculated according to the Gaddum-Schild Equation (based on Law of Mass Action).

$$DR - 1 = [B] \times K_B$$

DR = dose ratio
[B] = molar concentration of compound

Rabbit Aorta System

Spiral strips of thoracic aorta are suspended in Kreb's-Henseleit solution and aerated with 95% O$_2$/5% CO$_2$ at 37° C. Tension changes are recorded with a Grass FTO3 force transducer. Initially, cumulative dose response curves to 11,9-(epoxymethano) PGH$_2$ (2×10$^{-9}$, 1×10$^{-8}$, 5×10$^{-8}$ and 2.5×10$^{-7}$ M) are obtained. In a second experiment the individual compounds are added 30 mins previous to the addition of the series of agonist doses. Affinity constants are calculated as above.

Results typical of those obtained for the various compounds of Table 1 are shown in Table 3. As a standard of comparison, the affinity constant of the potent muscarinic receptor antagonist atrophine is 1×10$^9$ liters/mole.

TABLE 3

| COMPOUND | AFFINITY CONSTANTS × 10$^{-5}$ liters/mole | |
|---|---|---|
|  | Human Platelets | Rabbit Aorta |
| —C$_6$H$_4$—F | 2.1 | 7.8 |
| —C$_6$H$_4$—N(CH$_3$)$_2$ | 1.0 | <2.5 |
| —C$_6$H$_4$—OCH$_3$ | — | 2.0 |
| —CH$_2$—C$_6$H$_5$ | — | 6.7 |
| —CH(—C$_6$H$_5$)$_2$ | 7.2$^{(1)}$ | 39 |
| —CH$_2$—CH(—C$_6$H$_5$)$_2$ | 20 | 6.6 |
| —CH$_2$—O—C$_6$H$_5$ | 0.52 | 3.7 |
| —NH—C$_6$H$_5$ | 7.0 | 13 |
| —NH—C$_6$H$_5$ $^{(2)}$ | 6.9 | 8.3 |

$^{(1)}$Slight antagonism of ADP; K$_B$(ADP) = 1.2 × 10$^5$
The other compounds do not block ADP, having K$_B$(ADP) of <0.25 × 10$^5$.
$^{(2)}$Double bond in substituent at 5-position is reduced in this compound.

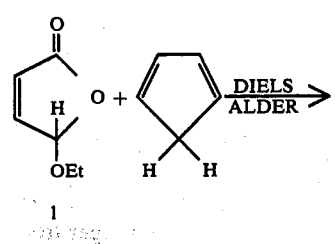

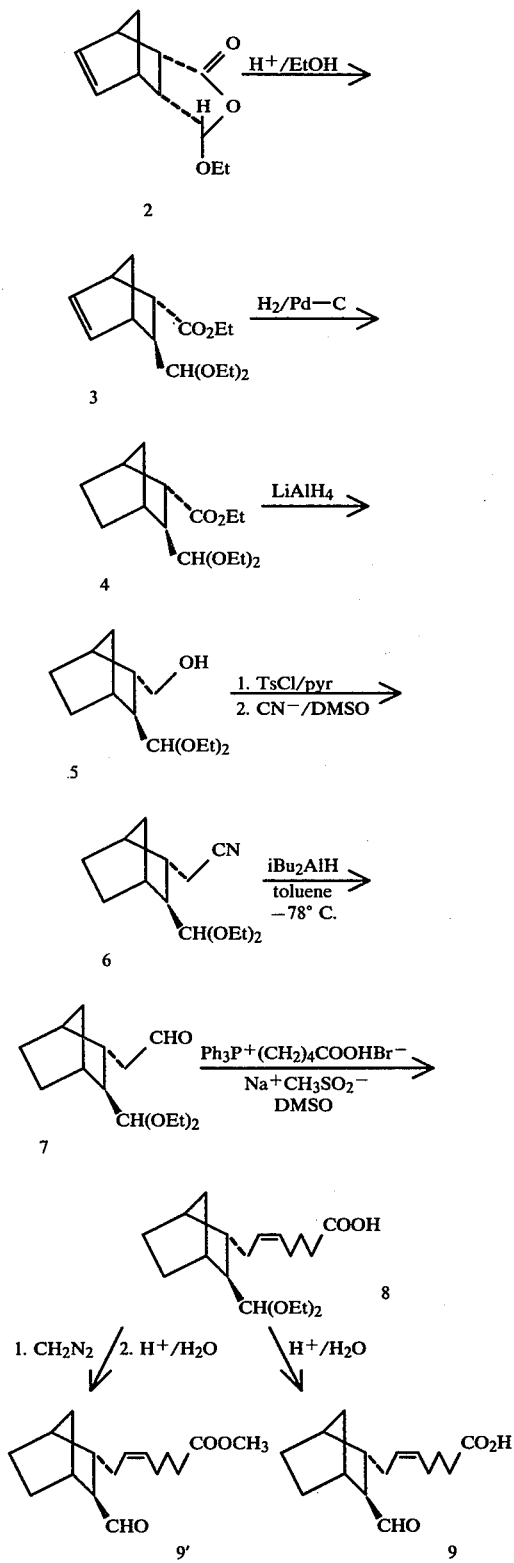

We claim:
1. A compound which is a bicyclo(2,2,1)heptane or hept-2Z-ene which is substituted at the 5-position by a group of the formula —R¹—COQ, where R¹ is selected from the group consisting of C$_4$–C$_8$ alkyl; —CH$_2$—CH=CH—(CH$_2$)$_m$—, wherein m is an integer from 1 to 5; —CH$_2$—CH$_2$—CH=CH(CH$_2$)$_n$—, where n is an integer from 0 to 4; —X—(CH$_2$)$_p$—, where p is an integer from 3 to 7; —CH$_2$—X—(CH$_2$)$_q$—, where q is an integer from 2 to 6; —CH$_2$—CH$_2$—X—(CH$_2$)$_m$—, and —CH=CH—(CH$_2$)$_3$—;
  wherein X is —O— or —S—;
  COQ is COOH, a physiologically acceptable carboxylate salt, a branched or unbranched C$_1$–C$_5$ alkyl ester or CONHSO$_2$CH$_3$;
  and wherein said bicyclo(2,2,1)heptane or hept-2Z-ene is substituted at the 6-position by a grouping of the formula:

—C(R)=NNHCO—(NH)$_a$—R';

wherein R is selected from the group consisting of hydrogen, unsubstituted C$_1$–C$_{10}$ branched or unbranched aliphatic hydrocarbon residues, and C$_1$–C$_{10}$ aliphatic hydrocarbon residues substituted by Ar, where Ar represents a monocyclic aromatic hydrocarbon or pyridyl residue, or such a residue substituted by one or more substituents selected from the group consisting of halogen, halogen substituted branched or unbranched C$_1$–C$_5$ alkyl groups, sulphonamido groups, amino groups, hydroxy and C$_1$–C$_{10}$ alkoxy;
  a is 0 or 1; and
  R' is selected from the group consisting of unsubstituted C$_1$–C$_{10}$ branched or unbranched aliphatic hydrocarbon residues, Ar and C$_1$–C$_{10}$ branched or unbranched aliphatic hydrocarbon residues substituted by —Ar, —OAr, or —SAr.

2. A compound according to claim 1 in which the substituent at the 5-position is (Z—)CH$_2$—CH=CH—CH$_2$CH$_2$CH$_2$—COQ.

3. A compound according to claim 1 in which the substituent at the 5-position is CH$_2$—CH$_2$—CH$_2$—CH$_2$—CH$_2$—CH$_2$—COQ.

4. A compound according to claims 2 or 3, wherein COQ is COOH or a physiologically acceptable carboxylate salt.

5. A compound according to claim 1, in which R is hydrogen.

6. A compound according to claim 1 in which a is 1.

7. A compound according to claim 1 in which R' is Ar or a C$_1$–C$_{10}$ aliphatic hydrocarbon residue substituted by Ar, —OAr or —SAr.

8. A compound according to claim 1 in which R' is a C$_1$–C$_{10}$ aliphatic hydrocarbon residue substituted by a single group selected from the groups Ar, —OAr and —SAr, or substituted by a group Ar and additionally by a group selected from Ar, —OAr and —SAr.

9. A compound according to claim 8 in which R' is a substituted C$_1$–C$_3$ aliphatic hydrocarbon residue.

10. A compound according to claim 1 in which the Ar residue or residues are a phenyl group or a phenyl group having one or more substituents selected from C$_1$–C$_{10}$ alkoxy, amino groups, halogen and halogen substituted, unbranched or branched C$_1$–C$_5$ alkyl groups.

11. A compound according to claim 10, in which said substituent(s) are methoxy, dimethylamino, chloro, fluoro or trifluoromethyl.

12. A compound according to claim 1 being a bicyclo (2,2,1) heptane.

13. A compound according to claim 8 wherein the aliphatic hydrocarbon residue is substituted directly by two phenyl groups or substituted phenyl groups.

14. A compound according to claim 1, in which the configuration about any double bond in the 5-substituent is cis.

15. A compound according to claim 1, in which the 5- and 6-substituents are in trans relationship.

16. A compound according to claim 1 in which the stereochemistry is such that the 5-substituent is oppositely disposed to the bridging methylene group.

17. A pharmaceutical composition comprising an amount effective to produce thromboxane antagonism, of a compound according to claim 1 as an active ingredient thereof, in combination with a physiologically acceptable diluent or carrier.

18. A compound according to claim 1, in which R is an unsubstituted $C_1$–$C_3$ aliphatic hydrocarbon residue or a $C_1$–$C_3$ aliphatic hydrocarbon residue substituted by Ar.

19. A compound according to claim 18, in which R is methyl.

20. A compound according to claim 7, in which R' is Ar or contains one or more residues Ar which are selected from unsubstituted phenyl groups and phenyl groups substituted by one or more substituents selected from the group consisting of halogen, halogen substituted unbranched or branched $C_1$–$C_5$ alkyl groups, sulphonamido groups, amino groups, hydroxy and $C_1$–$C_{10}$ alkoxy.

21. A compound according to claim 20, in which Ar or the residues Ar are an unsubstituted phenyl group or groups.

22. A compound according to claim 1, in which R' is an aliphatic hydrocarbon residue terminally substituted by an unsubstituted phenyl group or groups or a phenyl group or groups substituted by one or more substituents as therein, the aliphatic hydrocarbon residue being $C_1$–$C_3$ when having a=0, being $C_1$–$C_3$ when having a=1 and being substituted directly by said group or groups, and being $C_2$–$C_3$ when having a=1 and being substituted by said group or one of said groups through an oxygen or sulphur atom.

23. A compound according to claim 1 being 5-endo-(6'-carboxyhex-2'Z-enyl)-6-exo-hydrazonomethylbicyclo(2,2,1)heptane N-substituted at the hydrazonomethyl group by a substituent on the nitrogen atom thereof which is selected from the group consisting of p-fluorobenzoyl, p-methoxybenzoyl, p-dimethylaminobenzoyl, pehnylacetyl, diphenylacetyl, 3,3-diphenylpropionyl, phenoxyacetyl and pentanoyl.

24. A compound according to claim 1 selected from the group consisting of 5-endo-(6'-carboxyhex-2'Z-enyl)-6-exo-(N-p-fluorobenzoylhydrazonomethyl)-bicyclo(2,2,1)heptane, 5-endo-(6'-carboxyhex-2'Z-enyl)-6-exo(N-p-fluorobenzoylhydrazonomethyl)-bicyclo(2,2,1)hept-2Z-ene, 5-endo-(6'-carboxyhex-2'Z-enyl)-6-exo-(1'-(p-fluorobenzoyl-hydrazono)-ethyl)-bicyclo (2,2,1)heptane, 5-endo-(6'-carboxyhex-2'Z-enyl)-6-exo-{1'-(N-(phenylcarbamoyl)-hydrazono)-ethyl}-bicyclo(2,2,1)heptane, and 5-endo-(6'-carboxyhexyl)-6-exo-(N-(phenylcarbamoyl)-hydrazonomethyl)-bicyclo(2,2,1)heptane.

25. A method of treating thrombotic disorders, anaphylactic disease states and conditions requiring anti-inflammatory treatment in patients which comprises administering to the patient an amount of a compound according to claim 1 which is effective to inhibit thromboxane activity in the patient.

26. A compound according to claim 1, in which $R^1$ is $C_5$–$C_7$ alkyl; m is an integer from 2 to 4; n is an integer from 1 to 3; p is an integer from 4 to 6, and q is an integer from 3 to 5.

27. A compound according to claim 1 in which any aliphatic hydrocarbon residue is a $C_1$–$C_5$ alkyl group.

28. A compound according to claim 1, in which R' is an unsubstituted phenyl, pyrid-2-yl, pyrid-3-yl or pyrid-4-yl group or such a group substituted by one or more substituents as therein.

29. A compound according to claim 10, in which the substituents are selected from $C_1$–$C_5$ alkoxy, amino groups, halogen and halogen substituted methyl groups.

30. A compound according to claim 1 being a bicyclo(2,2,1)heptane or bicyclo(2,2,1)hept-2Z-ene having a 5-endo substituent which is (Z—)—$CH_2$—CH═CH—$CH_2$—$CH_2$—$CH_2$—COQ or $CH_2$—$CH_2$—$CH_2$—$CH_2$—$CH_2$—$CH_2$—COQ and 6-exo-substituent which is a hydrazonomethyl or a 1'-hydrazonoethyl group that is itself N-substituted by a substituent selected from the group consisting of benzoyl, p-fluorobenzoyl, p-methoxybenzoyl, p-dimethylaminobenzoyl, phenylacetyl, diphenylacetyl, 3,3-diphenylpropionyl, phenoxyacetyl, phenoxypropionyl, pentanoyl, phenylcarbamoyl, p-fluorophenylcarbamoyl, p-methoxyphenylcarbamoyl, p-dimethylaminophenylcarbamoyl, benzylcarbamoyl, diphenylmethylcarbamoyl, 2,2-diphenylethylcarbamoyl, phenoxyethylcarbamoyl and n-butylcarbamoyl.

31. 5-endo-(6'-Carboxyhex-2'Z-enyl)-6-exo-(N-(phenylcarbamoyl)-hydrazonomethyl)-bicyclo(2,2,1)heptane.

32. 5-endo-(6'-Carboxyhex-2'Z-enyl)-6-exo-(N-diphenylacetylhydrazonomethyl)-bicyclo(2,2,1)heptane.

* * * * *